US012576185B2

(12) United States Patent
Jang et al.

(10) Patent No.: US 12,576,185 B2
(45) **Date of Patent: \*Mar. 17, 2026**

(54) HYALURONIC ACID FILLER HAVING HIGH VISCOELASTICITY AND HIGH COHESIVENESS

(71) Applicant: LYV Sciences Co., Ltd., Iksan-si (KR)

(72) Inventors: Cheol Jang, Daejeon (KR); Chung Lee, Daejeon (KR); Ji Sun Kim, Daejeon (KR); Hyun Tae Jung, Daejeon (KR); Chang Hyun Lee, Daejeon (KR); Jineon So, Daejeon (KR); Hwayoun Ree, Daejeon (KR)

(73) Assignee: LYV Sciences Co., Ltd., Iksan-si (KR)

( * ) Notice: Subject to any disclaimer, the term of this patent is extended or adjusted under 35 U.S.C. 154(b) by 1039 days.

This patent is subject to a terminal disclaimer.

(21) Appl. No.: 17/258,274

(22) PCT Filed: Jul. 8, 2019

(86) PCT No.: PCT/KR2019/008374
§ 371 (c)(1),
(2) Date: Jan. 6, 2021

(87) PCT Pub. No.: WO2020/009555
PCT Pub. Date: Jan. 9, 2020

(65) Prior Publication Data
US 2021/0268143 A1      Sep. 2, 2021

(30) Foreign Application Priority Data
Jul. 6, 2018      (KR) ........................ 10-2018-0078989

(51) Int. Cl.
*A61L 27/20* (2006.01)
*A61L 27/52* (2006.01)
(Continued)

(52) U.S. Cl.
CPC ............... *A61L 27/20* (2013.01); *A61L 27/52* (2013.01); *A61L 27/54* (2013.01); *C08L 5/08* (2013.01);
(Continued)

(58) Field of Classification Search
None
See application file for complete search history.

(56) References Cited

U.S. PATENT DOCUMENTS 4,582,865 A      4/1986  Balazs et al.
5,827,937 A     10/1998  Agerup
(Continued)

FOREIGN PATENT DOCUMENTS

CN      103285423 A      9/2013
CN      106397846 A      2/2017
(Continued)

OTHER PUBLICATIONS

Cosmetics Challenge. https://assets.bmctoday.net/practicaldermatology/pdfs/PD1110%20CosmChallenge.pdf. Published: Nov. 2010.*
(Continued)

*Primary Examiner* — Nicole P Babson
*Assistant Examiner* — Lori K Mattison
(74) *Attorney, Agent, or Firm* — ROTHWELL, FIGG, ERNST & MANBECK, P.C.

(57) ABSTRACT

The hyaluronic acid filler according to the present invention exhibits improved high viscoelastic flow characteristics, and has advantages of monophasic hyaluronic acid fillers and biphasic hyaluronic acid fillers together, and therefore it maintains the shape while having low moving possibility when injecting into skin, and thus it is excellent when used for improving wrinkles, augmentation of soft tissues such as cheeks, breast, nose, lips and hips, etc., and correcting contours, and the duration time in the human body is (Continued)

increased and side effects are small, even if a small amount of crosslinking agent is used during the preparation process.

10 Claims, 1 Drawing Sheet

(51) Int. Cl.
  A61L 27/54 (2006.01)
  C08L 5/08 (2006.01)
(52) U.S. Cl.
  CPC ..... *A61L 2300/402* (2013.01); *A61L 2400/06* (2013.01); *A61L 2430/34* (2013.01)

(56) References Cited

U.S. PATENT DOCUMENTS

| | | |
|---|---|---|
| 2010/0255068 A1 | 10/2010 | Stroumpoulis et al. |
| 2012/0071437 A1 | 3/2012 | Stroumpoulis et al. |
| 2013/0131011 A1 | 5/2013 | Lebreton |
| 2014/0039062 A1 | 2/2014 | Stroumpoulis et al. |

FOREIGN PATENT DOCUMENTS

| | | |
|---|---|---|
| CN | 106589424 A | 4/2017 |
| KR | 10-1239037 B1 | 3/2013 |
| KR | 10-2014-0096028 A | 8/2014 |
| KR | 10-2015-0029578 A | 3/2015 |
| KR | 10-1660211 B1 | 9/2016 |
| KR | 10-1769739 B1 | 8/2017 |
| RU | 2653729 C2 | 5/2018 |
| TW | I430815 B | 3/2014 |
| WO | WO-2013123275 A1 * | 8/2013 ........... A61K 31/195 |
| WO | 2016-005785 A1 | 1/2016 |
| WO | 2016-051219 A1 | 4/2016 |
| WO | WO-2016128550 A1 * | 8/2016 ........... A61F 2/0059 |
| WO | 2017-213404 A1 | 12/2017 |
| WO | 2016-074794 A1 | 5/2019 |

OTHER PUBLICATIONS

Sutyagin V. M. et al. Chemistry and Physics of polymers: Training manual.—Tomsk (2003): TPU Publishing House, pp. 132, 140, 142, 151 and 173, with English translation (11 pages).

Extended European Search Report dated Jul. 15, 2021, of the corresponding European Patent Application No. 19830465.1, 10 pages.

International Search Report dated Oct. 14, 2019, issued in the corresponding International Application No. PCT/KR2019/008374, 6 pages.

Cowman et al., "Viscoelastic Properties of Hyaluronan in Physiological Conditions", F1000Research, 2015, vol. 4, No. 622, 13 pages.

Sheehan et al., "Effect of the cations sodium, potassium and calcium on the interaction of hyaluronate chains: a light scattering and viscometric study", International Journal of Biological Macromolecules, 1983, vol. 5, No. 4, pp. 222-228.

Micheels, et al., "Effect of Different Crosslinking Technologies on Hyaluronic Acid Behavior: A Visual and Microscopic Study of Seven Hyaluronic Acid Gels", Journal of Drugs in Dermatology: JDD, 2016, vol. 15, Issue 5, pp. 600-606.

* cited by examiner

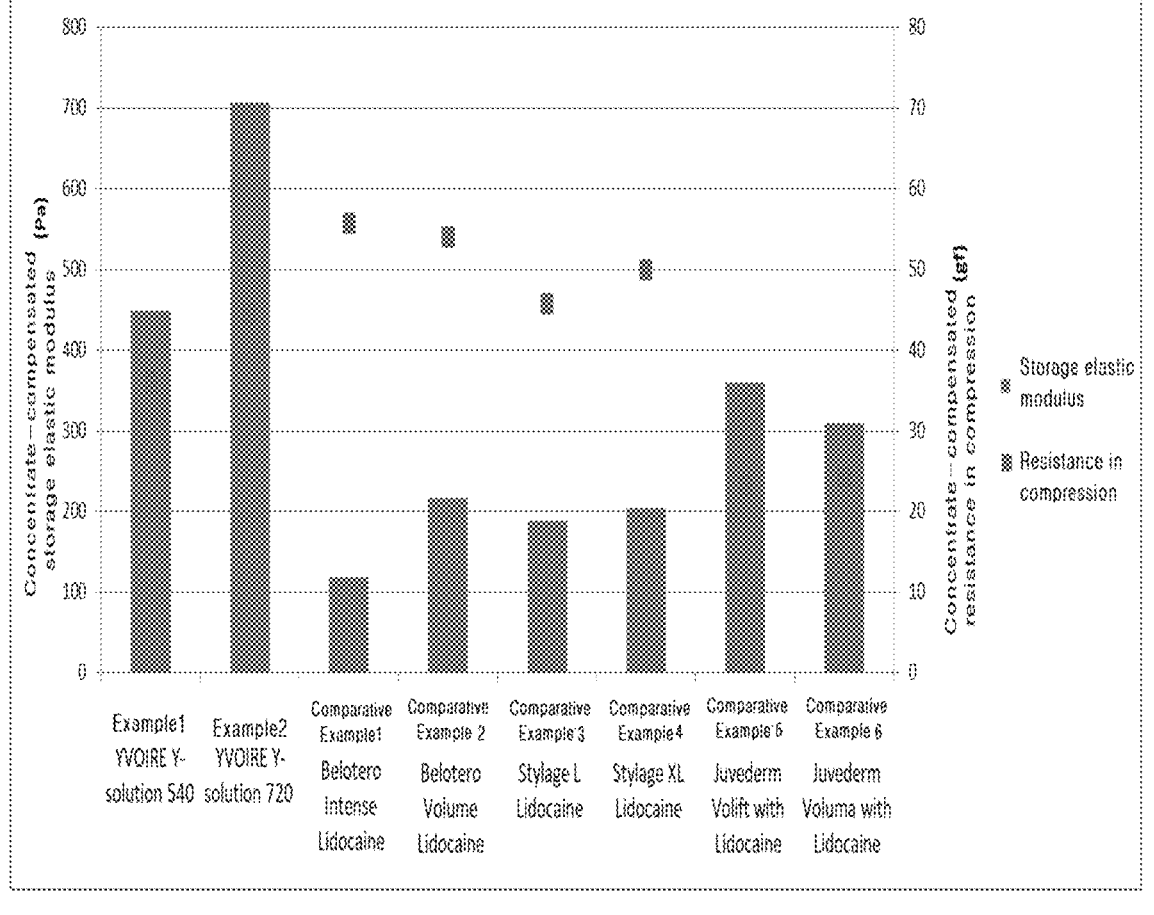

HYALURONIC ACID FILLER HAVING HIGH VISCOELASTICITY AND HIGH COHESIVENESS

TECHNICAL FIELD

Cross-Reference with Related Application(s)

The present application is a 35 U.S.C. 371 National Phase Entry Application from PCT/KR2019/008374, filed on Jul. 8, 2019, designating the United States, which claims the benefit of priority based on Korean Patent Application No. 10-2018-0078989 filed on Jul. 6, 2018, the entire contents of which are incorporated herein by reference.

The present invention relates to a hyaluronic acid filler, and more specifically, relates to a hyaluronic acid filler having high cohesivity of monophasic hyaluronic acid (HA) fillers and high elasticity of biphasic hyaluronic acid fillers simultaneously and a method for preparing thereof.

BACKGROUND OF THE INVENTION

Tissue of human skin maintains its structure by extracellular matrix including proteins such as collagen, elastin and the like and glycosaminoglycans, but when defects of soft-tissue occur due to external shock, diseases or aging and so on, tissue enhancement such as soft-tissue enhancement has been used for medical and cosmetic purposes. This enhancement has been done surgically through plastic surgery, or has restored and corrected its shape in a non-surgical manner by injecting biological tissue or synthetic polymer chemicals into the area to increase and expand the volume of soft-tissue. Then, a substance, which is a component similar to skin tissue and is inserted into a specific site to expand soft-tissue, and thereby it expands the volume of cheeks, lips, breast, hips, etc. cosmetically and is used for anti-wrinkle or contour correction through reduction of fine wrinkles and deep wrinkles of skin, is called a soft tissue augmentation material, and it is generally called a dermal filler. The first generation dermal filler primally developed in connection with this filler includes products such as Zyderm and Zyplast prepared by extracting animal proteins derived from animals, that is, cows or pigs, etc., and Cosmoderm or Cosmoplast using human collagen, and the like, but they have been rarely operated recently because of short duration of the effect and inconvenience of performing a skin sensitization test one month before the procedure.

The second generation filler is a hyaluronic acid (hereinafter, also referred to as 'HA') filler and has longer duration of the effect than the collagen filler and consists of polysaccharides similar to human components, N-acetyl-D-glucosamine and D-glucuronic acid, and therefore it has less side effects and is easy to procedure and removal, and it is possible to maintain the skin moisture, volume and elasticity by attracting water, and thus it has suitable advantages as a filler for skin.

However, the hyaluronic acid itself shows a short half-life of only a few hours in the human body, and therefore there is a limitation in application, and thus researches have been conducted to increase the half-life (internal persistence) through crosslinking. For example, U.S. Pat. No. 4,582,865 discloses a hyaluronic acid derivative crosslinked using divinylsulfone (DVS) as a crosslinking agent, and its hydrogel form has been marketed under the trade name Hylaform®, and U.S. Pat. No. 5,827,937 discloses a method for preparing a hyaluronic acid derivative crosslinked product using a multifunctional epoxy compound as a crosslinking agent, and among them, Restylane®, a hydrogen form of a hyaluronic acid crosslinked product prepared using 1,4-butanediol diglycidyl ether (BDDE) as a crosslinking agent has been approved by U.S. FDA and is available worldwide as a filler for tissue enhancement.

Such a crosslinked hyaluronic acid filler includes a filler made of a single-phase (monophasic HA filler) and a filler made of dual-phase (biphasic HA filler). The monophasic hyaluronic acid filler is prepared using a homogeneous liquid-like hydrogel comprising a crosslinked hyaluronic acid, and thus it generally has low elasticity and high cohesivity. Accordingly, when the monophasic hyaluronic acid filler is injected into skin, it is unlikely to deviate from the injected site, but there are problems that the injected form is not maintained for a long time and the shape (form) retention period is only about 2 months after the procedure.

The biphasic hyaluronic acid filler is prepared by mixing crosslinked hyaluronic acid particles alone or with non-crosslinked hyaluronic acid close to liquid (untreated non-crosslinked hyaluronic acid (linear HA), and therefore it generally has high elasticity and low cohesivity. Accordingly, when the biphasic HA filler is injected, it may maintain its shape for a long time, but there is a problem that there is a high possibility of deviating from the injected site. A representative example of the biphasic HA filler is the aforementioned Restylane® (Galderma product).

As such, the monophasic HA filler and biphasic HA filler have advantages and disadvantages, respectively, and conventionally, there is an example in which the above fillers are mixed to have all the properties of the monophasic hyaluronic acid filler and biphasic hyaluronic acid filler, but in this case, the advantages of the monophasic hyaluronic acid filler and biphasic hyaluronic acid filler are rather reduced together, and therefore it is not suitable as a filler. Thus, there is a need for a filler which can maintain its shape for a long time while having a low possibility of deviating from the injected site.

BRIEF SUMMARY OF THE INVENTION

The present invention provides a filler having high viscoelasticity and cohesivity as advantages of monophasic HA fillers and biphasic HA fillers, that is, a filler which can maintain the shape for a long time while being less likely to escape from the injected site, and can be injected into human skin to be used for improving wrinkles and shaping.

The present invention also provides a method for preparing such a filler.

DETAILED DESCRIPTION OF THE INVENTION

The present application has been invented to solve the above problems of the prior art, and when a hyaluronic acid meets conditions such as specific molecular weight and degree of crosslinking, it has high cohesivity of the monophasic filler and high viscoelasticity of the biphasic filler simultaneously, and accordingly it has been confirmed that it can be easily made into a desired form and can be maintained for a desired period when injected into skin, thereby completing the present invention.

Accordingly, as one aspect, the present invention relates to a hyaluronic acid filler which has high viscoelasticity and cohesivity, thereby showing properties of both monophasic filler and biphasic filler, a pre-filled syringe filled with the filler, a biomaterial for soft tissue augmentation containing the filler or a method for improving wrinkles comprising injecting it into biological tissue.

The hyaluronic acid (hereinafter, also referred to as 'HA') comprised in the filler of the present invention is a biopolymer material in which repeating units consisting of N-acetyl-D-glucosamine and D-glucuronic acid are linearly connected, and it is present a lot in vitreous humor of eyes, synovial fluid of joint, cockscomb, and the like, and it has been widely used for medical and medical appliance such as ophthalmic surgical aids, joint function improving agents, drug delivery materials, eye drops, anti-wrinkle agents, or cosmetics, as it has excellent biocompatibility. Specifically, the hyaluronic acid comprised in the filler of the present invention may mean its salt in addition to the hyaluronic acid. The salt of the hyaluronic acid includes for example, inorganic salts such as sodium hyaluronic acid, potassium hyaluronic acid, calcium hyaluronic acid, magnesium hyaluronic acid, zinc hyaluronic acid, cobalt hyaluronic acid, and the like, and organic salts such as tetrabutyl ammonium hyaluronic acid, and so on all, but not limited thereto.

In addition, preferably, the hyaluronic acid or its salt may be crosslinked by an appropriate crosslinking agent.

The crosslinked hyaluronic acid derivative may be prepared by crosslinking the above hyaluronic acid itself or its salt using a crosslinking agent. For crosslinking, a method using a crosslinking agent under an alkaline aqueous solution may be used. The alkaline aqueous solution includes NaOH, KOH, preferably, NaOH aqueous solution, but not limited thereto. Then, in case of NaOH aqueous solution, it may be used at a concentration of 0.1N to 0.5N. The crosslinked hyaluronic acid comprised in the filler of the present invention particularly shows high viscoelasticity and cohesivity even when a crosslinking agent at a low concentration and in a small amount is used. The concentration of the crosslinking agent may be 1 to 10 mol % relative to 1 mole of N-acetyl-D-glucosamine and D-glucuronic acid that is a unit in the hyaluronic acid or its salt.

The crosslinking agent is a compound comprising two or more of epoxy functional groups and it may vary, and as a preferable example, it includes butanediol diglycidyl ether (1,4-butanediol diglycidyl ether: BDDE), ethylene glycol diglycidyl ether (EGDGE), hexanediol diglycidyl ether (1,6-hexanediol diglycidyl ether), propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, bisepoxypropoxy ethylene (1,2-(bis(2,3-epoxypropoxy)ethylene), pentaerythritol polyglycidyl ether and sorbitol polyglycidyl ether, and the like, and among them, biepoxide-based 1,4-butanediol glycidyl ether is particularly preferable in aspect to low toxicity.

Herein, the term "degree of modification (MOD)" means a degree of modification of hyaluronic acid calculated by a numerical value (n) showing the number of moles of the crosslinking agent (for example, BDDE) bound to the whole hyaluronic acid molecule relative to the number of moles of N-acetyl-D-glucosamine in the unit of the hyaluronic acid (N-acetyl-D-glucosamine (GlcNAc)+D-glucuronic acid), and it may be represented by the following Equation 1.

$$\text{Degree of modification (MOD) (\%)} = \text{total number of moles of crosslinking agent/total number of moles of N-acetyl-D-glucosamine} \times 100. \quad \text{[Equation 1]}$$

In the present invention, particularly, it is characterized in that such a degree of modification shows a range of 1 to 7%, preferably, a range of 3 to 5%, through crosslinking by the above crosslinking agent.

In addition, herein, the term "crosslinking ratio (CrR)" means the ratio of the number of moles of the crosslinked crosslinking agent relative to the number of moles of the total crosslinking agent, and it may be represented by the following Equation 2.

$$\text{Crosslinking ratio} = \text{number of moles of crosslinked crosslinking agent/number of moles of total crosslinking agent} \quad \text{[Equation 2]}$$

In the present invention, particularly, it is characterized by showing a range of 0.1 to 0.2, preferably 0.14 to 0.17 through crosslinking. Preferably, the hyaluronic acid filler according to the present invention has a characteristic of synergistically showing properties of monophasic and biphasic fillers at the same time by having the above MOD and CrR ranges.

Herein, the molecular weight of the crosslinked hyaluronic acid may be 2,500,000 Da or more, preferably 2,500,000 to 3,500,000 Da.

The term "elasticity" used herein means a property as solid when applying force to an object, that is, a property of changing the form when applying force, but returning to the original form when removing force. This elasticity is represented by storage modulus (G': elastic modulus), and its unit is pascal (Pa). In addition, the term, viscosity used herein means a property as liquid, that is, the quantity that desscrobes a fluid's resistance to flow. This viscosity may be represented by loss modulus (G": viscous modulus) and its unit is pascal (Pa).

The term, viscoelasticity used herein means having such elastic deformation and viscosity simultaneously, when applying force to an object, and the crosslinked hyaluronic acid hydrogels comprised in the filler as the present invention exhibit both viscosity and elasticity, and therefore they have viscoelasticity. This viscoelasticity may be evaluated by complex viscosity which can reflect both storage elastic modulus (G') and loss elastic modulus (G"), and its unit is centipoise (cP).

The term, cohesivity used herein is attraction (adhesion) acting between filler particles, and it may cause filler particles to agglomerate together. The higher this cohesivity is, the bigger the force that can support tissue into which the filler is injected is. Commonly, the cohesivity may be indirectly measured by a compression test, and it is measured as resistance when compressed at a certain rate after loading on a rheometer, and its unit is gf (gram force).

Generally, the hyaluronic acid filler in a monophasic form shows a cohesive gel, and therefore it has high cohesivity and low viscoelasticity. The example includes Juvederm® of Allergan. In addition, the hyaluronic acid filler in a biphasic form shows a particle form, and therefore it is characterized by having high viscoelasticity and low cohesivity. The example includes Restyane® of Galderma.

As described above, the hyaluronic acid filler in a monophasic form and the hyaluronic acid filler in a biphasic form have respective advantages and disadvantages.

The hyaluronic acid according to the present invention has high viscoelasticity and cohesivity, and thus it is characterized by having properties of the monophasic filler and properties of the biphasic filler simultaneously. Preferably, the hyaluronic acid filler according to the present invention exhibits complex viscosity (viscoelasticity) of $6 \times 10^4$ or more, preferably 60,000 to 130,000 cP, at an angular velocity of 1 Hz, when measured by a rheometer, and exhibits a storage elastic modulus G' of 400 Pa or more, preferably, 400 to 800 Pa, and exhibits cohesivity of 30 gf, preferably 30 to 60 gf.

In addition, a hyaluronic acid particle, preferably, a cross-linked hyaluronic acid particle, in the hyaluronic acid filler according to the present invention, may show various shapes, but preferably, it may be in a sphere shape. Furthermore, the average diameter of this particle may be 300 to 400 μm.

In a preferable aspect, the hyaluronic acid filler according to the present invention may comprise a hyaluronic acid of 1 to 3% by weight based on the total filler weight. In addition, the hyaluronic acid filler according to the present invention may further comprise water, an anesthetic or a combination thereof, in addition to the hyaluronic acid.

The anesthetic comprises one or more kinds of anesthetics, preferably, local anesthetics, known in the art, and the concentration of one or more of anesthetics is an effective amount for alleviating symptoms to be experienced when injecting a composition. The example of the anesthetic may be selected from the group consisting of ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine and salts thereof. In one embodiment, the anesthetic may be lidocaine, for example, a form of lidocaine hydrochloride.

For the hyaluronic acid filler according to the present invention, the concentration of the anesthetic comprised in the filler may be about 0.1% by weight to about 1.0% by weight based on the total weight of the filler, for example, about 0.2% by weight to about 0.5% by weight of the composition.

The concentration of the anesthetic in the filler described herein may be therapeutically effective, and this means a concentration which is unharmful to a patient and is suitable for providing advantages in an aspect of convenience of procedures and compliance of patients.

In addition, the filler according to the present invention may further comprise a buffer solution, and the buffer solution may use anything used for preparation of hyaluronic acid hydrogels without limitation. A preferable example of the buffer solution may be a buffer solution comprising one or more kinds selected from the group consisting of citric acid, sodium monohydrogen phosphate, sodium dihydrogen phosphate, acetic acid, diethyl barbituric acid, sodium acetate, TAPS (tris(hydroxymethyl)methylamino) propanesulfonic acid), Bicine (2-bis(2-hydroxyethyl)amino) acetic acid), Tris (tris(hydroxymethyl) ammonium methane), Tricine (N-(2-hydroxy-1,1-bis(hydroxymethyl)ethyl)glycine), HEPES (4-(2-hydroxyethyl)-1-piperazine ethanesulphonic acid), TES (2-[[1,3-dihydroxy-2-(hydroxymethyl) propan-2-yl]amino] methanesulfonic acid) and PIPES (piperazine-N,N'-bis(2-ethanesulfonic acid), but not limited thereto. The content of the above components comprised in the buffer solution may be appropriately adjusted, but preferably, they may be comprised at a concentration of 0.3 to 2.0 g/L based on the buffer solution.

Moreover, the filler according to the present invention may further comprise a isotonic agent, and this isotonic agent may be used without limitation, as long as it is used for preparation of hyaluronic acid hydrogels. As a preferable isotonic agent, sodium chloride may be used, but not limited thereto. The content of the isotonic agent may be appropriately adjusted if necessary, and for example, it may be comprised in an amount of 7.0 to 9.0 g/L based on the buffer solution, but not limited thereto.

In one example according to the present invention, a buffer solution comprising sodium chloride, sodium monohydrogen phosphate and sodium dihydrogen phosphate in injection water was used.

As an additional aspect, the composition according to the present invention may further comprise acceptable components that can be comprised in preparation of a filler, in addition to the above components.

Furthermore, it is characterized in that a residual crosslinking agent in the hyaluronic acid filler having high viscoelasticity and cohesivity of the present invention is rarely comprised, and the residual crosslinking agent is preferably 0.5 ppm or less that is a detection limit.

This hyaluronic acid filler having high viscoelasticity and cohesivity according to the present invention may be very usefully used on a cosmetic or therapeutic purpose, by the present distinctive elastic property and cohesivity. As a specific example, this hyaluronic acid filler may be used for filling of biological tissue, anti-wrinkle by filling wrinkle, remodeling of the face, or restoration or increases of volume of soft-tissue such as lips, nose, hips, cheeks or breast, and the like, as a biomaterial for soft-tissue augmentation. The hyaluronic acid filler may be administered in an administration form appropriate for such uses, and preferably, it may be an injection.

As other aspect, the present invention relates to a preparation method of the above hyaluronic acid filler having high viscoelasticity and cohesivity comprising the following steps:

(a) preparing crosslinked hyaluronic acid hydrogels by adding a hyaluronic acid or its salt, a crosslinking agent to an alkaline aqueous solution and stirring and then reacting;

(b) cutting the hyaluronic acid hydrogels prepared in the step (a);

(c) preparing a buffer solution;

(d) washing and swelling the hyaluronic acid hydrogels cutted in the step (b) using the buffer solution prepared in the step (c);

(e) grinding the washed and swollen hyaluronic acid hydrogels in the step (d); and (f) filling the hydrogels prepared in the step (e) into a syringe and then sterilizing.

The step (a) is a step of preparing crosslinked hyaluronic acid hydrogels by crosslinking reacting a hyaluronic acid or its salt in an alkaline aqueous solution using a crosslinking agent, and as the matters related to the hyaluronic acid or its salt, crosslinking agent, and crosslinked hyaluronic acid hydrogel, the same applies to those mentioned in the hyaluronic acid filler.

The alkaline aqueous solution may use anything known as an alkaline aqueous solution suitable for preparation of hyaluronic acid hydrogels, without limitation, and for example, it may be NaOH, KOH, $NaHCO_3$, LiOH or a combination thereof, and preferably, it may be NaOH. The concentration of this alkaline aqueous solution may be 0.1 to 0.5 N, but not limited thereto. It may be 0.25N most preferably. It was confirmed that the hyaluronic acid hydrogels of the filler according to the present invention had the best physical properties after crosslinking under 0.25N NaOH basicity.

In addition, the concentration of the hyaluronic acid or its salt is a weight ratio of the hyaluronic acid or its salt based on the total weight of the mixture of the hyaluronic acid or its salt and alkaline aqueous solution, and it may be 10 to 25% by weight, and the concentration of the crosslinking agent is 1 to 10 mol % based on the unit of the added hyaluronic acid or its salt of 1 mole. When the concentration of the crosslinking agent is used at a high concentration over the above range, a filler with excessively high elasticity is obtained, and when the concentration is less than the above range, the elasticity is excessily low and therefore it is not possible to exhibit appropriate viscoelasticity. Specifically, the step (a) may be performed by mixing and stirring a hyaluronic acid or its salt, and a crosslinking agent and an alkaline aqueous solution to mix homogeneously. It may be performed at a temperature during crosslinking that is a room temperature or more, preferably in a temperature range of 25 to 40° C., for 15 to 22 hours.

The cutting process of the step (b) may use various known cutting processes of hyaluronic acid hydrogels. In one example, the crosslinked gel prepared after the reaction is obtained in a form of cake, and it may be divided into a half moon shape using a cutter such as a straw cutter and the like, and for example, it may be divided into six. Then, the cutting process may be performed by passing through (preferably 2 times or more) the gel divided as above using a preliminary grinder having constant intervals of blades.

The step (c) is a step of preparing a buffer solution used for washing and swelling the crosslinked hyaluronic acid hydrogels cutted in the step (b), and the buffer solution may be prepared by known preparation methods of a buffer solution. In addition, the buffer solution may further comprise an anesthetic additionally. In one specific embodiment of the present invention, the buffer solution was prepared by dissolving sodium monohydrogen phosphate hydrates, sodium dihydrogen phosphate hydrates, sodium chloride and lidocaine hydrochloride in a buffer tank filled with injection water.

The buffer solution may be used without limitation as long as it is used for preparation of hyaluronic acid hydrogels. The example of this preferable buffer solution may be a buffer solution comprising one or more kinds selected from the group consisting of citric acid, sodium monohydrogen phosphate, sodium dihydrogen phosphate, acetic acid, diethyl barbituric acid, sodium acetate, TAPS (tris(hydroxymethyl)methylamino) propanesulfonic acid), Bicine (2-bis(2-hydroxyethyl)amino) acetic acid), Tris (tris(hydroxymethyl) ammonium methane), Tricine (N-(2-hydroxy-1,1-bis(hydroxymethyl)ethyl)glycine), HEPES (4-(2-hydroxyethyl)-1-piperazine ethanesulphonic acid), TES (2-[1,3-dihydroxy-2-(hydroxymethyl) propan-2-yl]amino] methanesulfonic acid) and PIPES (piperazine-N,N'-bis(2-ethanesulfonic acid), but not limited thereto.

The step (d) is a step of washing and swelling the crosslinked hyaluronic acid hydrogels ground in the step (b) with the buffer solution prepared in the step (c), and this step (d) may be repeated once or two times or more. When completing washing and swelling, the washing solution may be removed.

The step (e) is a step of grinding the washed and swollen hydrogels, and this grinding may be performed by various grinding methods, but preferably, it may be extrusion grinding.

In addition, after the step (e), to filling the prepared hydrogels into a syringe and sterilizing, known filling and sterilizing methods may be used. For example, in case of sterilizing, an autoclave and the like may be used, but not limited thereto, and methods used for sterilization of a filler may be properly selected and used.

Advantageous Effects

The filler according to the present invention has the following effects. First, it can be useful as a filer having all the advantages of monophasic hyaluronic acid fillers and biphasic hyaluronic acid fillers, that is, a filler for enlarging the restore or volume of soft tissues such as cheeks, lips, chest, hips, etc., and improving wrinkles by reduction of fine wrinkles and deep wrinkles of skin or correcting contours, as it exhibits high viscoelasticity and cohesivity and thereby it can maintain the shape for a long time while being less likely to escape from the injected site.

BRIEF DESCRIPTION OF THE DRAWINGS

FIG. 1 is a graph showing the result of measuring the storage modulus and resistance in compression of the hyaluronic acid fillers according to Examples 1 and 2, and Comparative examples 1 to 6.

Hereinafter, the present invention will be described in more detail by examples. However, these examples are intended to illustrate the present invention exemplarily, and the scope of the present invention is not limited by these examples.

EXAMPLES

For preparation of the hyaluronic acid filler according to the present invention, the following process was conducted.

Sodium hyaluronic acid, sodium hydroxide, and BDDE (1,4-Butanediol Diglycidyl Ether), having a molecular weight of 2.5 MDa to 3.5 MDa were weighed. The concentration of sodium hyaluronic acid during the reaction was 15 wt %, and the mol % of BDDE was 4 mol % based on the unit of the added sodium hyaluronic acid (namely, N-acetyl-D-glucosamine and D-glucuronic acid) of 1 mol. Separately, a sodium hydroxide aqueous solution at a concentration of 0.25N was prepared and filtered. The weighed sodium hyaluronic acid, 0.25N sodium hydroxide aqueous solution and BDDE (1,4-Butanediol Diglycidyl Ether) were added to a mixer container and were mixed homogenously, and this mixer container was put in a constant-temperature waterbath and the crosslinking reaction was completed at a temperature of 30° C. overnight. Then, the crosslinked hyaluronic acid hydrogels in which the reaction was completed were preliminarily ground. On the other hand, a buffer solution was prepared by dissolving salts and an anesthetic in a buffer tank filled with injection water at concentrations of sodium monohydrogen phosphate hydrates (12 hydrates) 1.26 g/L, sodium dihydrogen phosphate hydrates (monohydrates) 0.46 g/L, sodium chloride 7 g/L and lidocaine hydrochloride 3 g/L.

A part of the buffer solution was considered as the primary buffer solution and it was transferred to a washing tank through a 0.22 (m filter, and the preliminarily ground hyaluronic acid gel prepared earlier was transferred to the washing tank filled with the primary buffer solution and then was stirred to primarily wash and swell the hyaluronic acid gel, and then when swelling was completed, the washing solution was removed. Then, the secondary buffer solution was transferred into a washing tank through a 0.22/m filter, and then it was stirred to secondarily wash and swell the hyaluronic acid gel. When the washing and swelling were completed, the washing solution was removed. Then, the tertiary buffer solution was transferred into a washing tank through a 0.22/mm filter, and then it was stirred to tertiarily wash and swell the hyaluronic acid gel. The washing solution was removed as soon as the washing and swelling was completed.

After completing the tertiary washing and swelling, whether the pH of the washing solution was in the neutral range was confirmed, and after cutting the hyaluronic acid gel in which washing and swelling was completed, it was transferred to an extruder tank and was weighed, and so as to reach a desired weight of the gel weight, the buffer solution was added to correct the primary content. When the primary content correction was completed, the hyaluronic acid gel was extruded and ground in the extruder tank. Then, the ground hyaluronic acid gel was transferred to a sterile tank and was homogenized, and then the content was measured and the buffer solution was added to conduct the secondary content correction. The hyaluronic acid gel in which the content correction was completed was heat-treated at a temperature of 121° C. or more, for 1 minute or more, and the hyaluronic acid gel before filling this was decompressed while stirring to conduct desaturation. Then, the hyaluronic acid gel in a fixed amount of filling was vacuumed/filled to each syringe and at the same time, it was stopped with a rubber stopper. The filled syringes were steam sterilized in a final sterilizer at a temperature of 121° C. or more for 8 minutes or more.

Example 2: Preparation of the Hyaluronic Acid Filler According to the Present Invention For preparation of the hyaluronic acid filler according to the present invention, the following process was conducted.

Sodium hyaluronic acid, sodium hydroxide, and BDDE (1,4-Butanediol Diglycidyl Ether), having a molecular weight of 2.5 MDa to 3.5 MDa were weighed. The concentration of sodium hyaluronic acid during the reaction was 16 wt %, and the mol % of BDDE was 4 mol % based on the unit of the added sodium hyaluronic acid (namely, N-acetyl-D-glucosamine and D-glucuronic acid) of 1 mol. Separately, a sodium hydroxide aqueous solution at a concentration of 0.25N was prepared and filtered. The weighed sodium hyaluronic acid, 0.25N sodium hydroxide aqueous solution and BDDE (1,4-Butanediol Diglycidyl Ether) were added to a mixer container and were mixed homogenously, and this mixer container was put in a constant-temperature waterbath and the crosslinking reaction was completed at a temperature of 30° C. overnight. Then, the crosslinked hyaluronic acid hydrogels in which the reaction was completed were preliminarily ground. On the other hand, a buffer solution was prepared by dissolving salts and an anesthetic in a buffer tank filled with injection water at concentrations of sodium monohydrogen phosphate hydrates (12 hydrates) 1.26 g/L, sodium dihydrogen phosphate hydrates (monohydrates) 0.46 g/L, sodium chloride 7 g/L and lidocaine hydrochloride 3 g/L.

A part of the buffer solution was considered as the primary buffer solution and it was transferred to a washing tank through a 0.22 μm filter, and the preliminarily cutted hyaluronic acid gel prepared earlier was transferred to the washing tank filled with the primary buffer solution and then was stirred to primarily wash and swell the hyaluronic acid gel, and then when swelling was completed, the washing solution was removed. Then, the secondary buffer solution was transferred into a washing tank through a 0.22 (m filter, and then it was stirred to secondarily wash and swell the hyaluronic acid gel. When the washing and swelling were completed, the washing solution was removed. Then, the tertiary buffer solution was transferred into a washing tank through a 0.22/filter, and then it was stirred to tertiarily wash and swell the hyaluronic acid gel. The washing solution was removed as soon as the washing and swelling was completed.

After completing the tertiary washing and swelling, whether the pH of the washing solution was in the neutral range was confirmed, and after grinding the hyaluronic acid gel in which washing and swelling was completed, it was transferred to an extruder tank and was weighed, and so as to reach a desired weight of the gel weight, the buffer solution was added to correct the primary content. When the primary content correction was completed, the hyaluronic acid gel was extruded and ground in the extruder tank. Then, the ground hyaluronic acid gel was transferred to a sterile tank and was homogenized, and then the content was measured and the buffer solution was added to conduct the secondary content correction. The hyaluronic acid gel in which the content correction was completed was heat-treated at a temperature of 121° C. or more, for 1 minute or more, and the hyaluronic acid gel before filling this was decompressed while stirring to conduct desaturation. Then, the hyaluronic acid gel in a fixed amount of filling was vacuumed/filled to each syringe and at the same time, it was stopped with a rubber stopper. The filled syringes were steam sterilized in a final sterilizer at a temperature of 121° C. or more for 10 minutes or more.

Experimental Example 1: Investigation of Viscoelasticity Properties of the Hyaluronic Acid Filler Prepared by the Present Invention For investigation of rheological properties of prepared Examples 1 and 2, analysis was conducted using a rheometer. For comparison with the filler of the present invention, viscoelasticity properties of commercially available filler preparations were also analyzed and compared. The commercially available filler preparations as comparative examples and analysis conditions were as follows.

Comparative Examples

Comparative example 1: Belotero Intense Lidocaine
Comparative example 2: Belotero Volume Lidocaine
Comparative example 3: Stylage L Lidocaine
Comparative example 4: Stylage XL Lidocaine
Comparative example 5: Juvederm Volift with Lidocaine
Comparative example 6: Juvederm Voluma with Lidocaine.

<Analysis Conditions>
Analysis Conditions of Oscillatory and Rotational Rheometer
In case of storage elastic modulus (G') and complex viscosity ($\eta^*$) test
  (1) Test equipment: Rheometer (Anton Paar Ltd., MCR301)
  (2) Frequency: 1 Hz
  (3) Temperature: 25° C.

11

12

(4) Strain: 4%

(5) Measuring geometry: 25 mm plate (9) Measuring gap: 1.0 mm

In case of resistance when compressed (Compression force)

(1) Test equipment: Rheometer (Anton Paar Ltd., MCR301)

(2) Gap: Initial position: 2.5 mm, Final position: 0.9 mm (3) Speed: 0.8 mm/min (4) Temperature: 25° C.

(5) Measuring geometry: 25 mm plate (9) Normal Force Measuring gap position: 1.5 mm Under the analysis conditions, the result values of the storage elastic modulus (G'), complex viscosity (n°) and resistance when compressed (Compression force) by frequency were shown in Table 1.

As confirmed in the Table 1, it is determined that Examples 1 and 2 according to the present invention exhibit excellent viscoelasticity compared to Comparative examples 1 to 6. Moreover, regarding cohesivity despite of showing properties of monophasic fillers and biphasic fillers simultaneously, they show excellent compression force than the monophasic fillers, Comparative examples 5 and 6. Furthermore, considering both viscoelasticity and cohesivity, it can be seen that Examples 1 and 2 according to the present invention show excellent physical properties compared to Comparative examples 1 to 6.

Experimental Example 2: Analysis of the Particle Size of the Hyaluronic Acid Hydrogels According to the Present Invention In order to confirm the particle size of the hyaluronic acid hydrogels of Examples 1 and 2 and Comparative examples

TABLE 1

| Example/ Comparative example | Present invention Example 1 | Example 2 | Belotero Comparative example 1 Belotero Intense Lidocaine | Belotero Comparative example 2 Belotero Volume Lidocaine | Stylage Comparative example 3 Stylage L Lidocaine | Stylage Comparative example 4 Stylage XL Lidocaine | Juvederm Comparative example 5 Juvederm Volift with Lidocaine | Juvederm Comparative example 6 Juvederm Voluma with Lidocaine |
|---|---|---|---|---|---|---|---|---|
| Concentration (mg/mL) | 20 | 20 | 25.5 | 26 | 24 | 26 | 17.5 | 20 |
| Storage elastic modulus (Pa, 1 Hz) | 448 | 707 | 149 | 280 | 225 | 264 | 314 | 310 |
| Complex viscosity ($\times 10^4$ cP, 1 Hz) | 7.18 | 11.3 | 2.54 | 4.57 | 3.65 | 4.28 | 5.08 | 4.97 |
| Compression force (gf) | 36 | 44 | 71 | 70 | 55 | 65 | 20 | 24 |
| Concentration-corrected storage elastic modulus (Pa, 1 Hz) (storage elastic modulus * (20/sample concentration)) | 448 | 707 | 117 | 215 | 188 | 203 | 359 | 310 |
| Concentration-corrected complex viscosity ($\times 10^4$ cP, 1 Hz) (complex viscosity * (20/sample concentration)) | 7.18 | 11.30 | 1.99 | 3.52 | 3.04 | 3.29 | 5.81 | 4.97 |
| Concentration-corrected Compression force (gf) (Compression force * (20/sample concentration)) | 36 | 44 | 56 | 54 | 46 | 50 | 23 | 24 |

1 to 6 and distribution, the following test was conducted. The result of this test was shown in Table 2.

<Analysis Conditions>

Analysis conditions of Laser diffraction particle size analyzer (1) Test equipment: Laser diffraction particle size analyzer (Malvern Ltd., Mastersizer 3000)

(2) Dispersant: 0.9% NaCl solution (3) Stirrer rpm: 1,000

(4) Laser obscuration: 5~25%

TABLE 2

| Example/ Compar- ative example | Present invention | | Belotero | | Stylage | | Juvederm | |
|---|---|---|---|---|---|---|---|---|
| | | | Comparative example 1 Belotero | Comparative example 2 Belotero | Comparative example 3 Stylage | Comparative example 4 Stylage | Comparative example 5 Juvederm Volift | Comparative example 6 Juvederm Voluma |
| | Example 1 | Example 2 | Intense Lidocaine | Volume Lidocaine | L Lidocaine | XL Lidocaine | with Lidocaine | with Lidocaine |
| Particle diameter, Dv(50) (μm) | 362 | 343 | 571 | 469 | 375 | 358 | 407 | 408 |

Experimental Example 3: Analysis ofDegree of Modification of the Hyaluronic Acid Hydrogels According to the Present Invention In order to confirm the degree of modification of the hyaluronic acid hydrogels of Examples 1 and 2 and Comparative examples 1 to 6, a test was performed under the following conditions. The result of this test was shown in Table 3.

<Analysis Conditions>

Analysis Conditions of Nuclear Magnetic Resonance (1) Test equipment: FT-NMR System (Jeol Ltd., ECA500/ECZ400S), (2) Pulse: 30° (3) Scans: 512

(4) Relaxation time (delay): 5 s (5) Temperature: 25° C.

TABLE 3

| Example/ Compar- ative example | Present invention | | Belotero | | Stylage | | Juvederm | |
|---|---|---|---|---|---|---|---|---|
| | | | Comparative example 1 Belotero | Comparative example 2 Belotero | Comparative example 3 Stylage | Comparative example 4 Stylage | Comparative example 5 Juvederm Volift | Comparative example 6 Juvederm Voluma |
| | Example 1 | Example 2 | Intense Lidocaine | Volume Lidocaine | L Lidocaine | XL Lidocaine | with Lidocaine | with Lidocaine |
| Degree of Modification (%) | 3.3 | 3.5 | 8.5 | 12.8 | 7.8 | 7.8 | 6.3 | 6 |

As can be seen in the Table 3, it can be seen that the hyaluronic acid fillers of Examples 1 and 2 according to the present invention exhibit a low degree of modification despite of showing excellent physical properties as confirmed earlier, and this means that it is very biocompatible as a filler showing excellent physical properties can be provided even when using a small amount of crosslinking agent during preparation of a filler.

The invention claimed is:

1. A hyaluronic acid hydrogel filler, comprising a cross-linked hyaluronic acid, wherein the filler has a complex viscosity of 60,000 to 130,000 cP at an angular velocity of 1 Hz as measured by a rheometer, a storage elastic modulus G' of 400 to 800 Pa, and a cohesivity of 30 to 60 gf, and wherein the crosslinked hyaluronic acid is one in which a hyaluronic acid having a molecular weight of 2,500, 000 Da or more is crosslinked and in the form of particles having an average diameter of 300 to 400 μm, a degree of modification (MOD) (%) of the hyaluronic acid as represented by Equation 1 following is in the range of 1 to 7%:

Degree of modification (%)=(total number of moles of crosslinking agent/total number of moles of N-acetyl-D-glucosamine)×100, and [Equation 1]

a crosslinking ratio (CrR) as represented by Equation 2 is in the range of 0.1 to 0.2:

Crosslinking ratio=number of moles of crosslinked crosslinking agent/number of moles of total crosslinking agent. [Equation 2]

2. The hyaluronic acid hydrogel filler according to claim 1, wherein the crosslinked hyaluronic acid is prepared by crosslinking a hyaluronic acid using a crosslinking agent selected from the group consisting of 1,4-butanediol diglycidyl ether, ethylene glycol diglycidyl ether (EGDGE), hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, bisepoxypropoxy ethylene, pentaerythritol polyglycidyl ether and sorbitol polyglycidyl ether.

3. The hyaluronic acid hydrogel filler according to claim 2, wherein the crosslinking agent is 1,4-butanediol diglycidyl ether.

4. The hyaluronic acid hydrogel filler according to claim 1, further comprising an anesthetic.

5. The hyaluronic acid hydrogel filler according to claim 4, wherein the anesthetic is lidocaine or a salt thereof.

6. A hyaluronic acid hydrogel filler, comprising a crosslinked hyaluronic acid, wherein the filler has a complex viscosity of 60,000 to 130,000 cP at an angular velocity of 1 Hz as measured by a rheometer, a storage elastic modulus G' of 400 to 800 Pa, and a cohesivity of 30 to 60 gf, wherein the filler comprises a crosslinking agent at a concentration of 1 to 10 mol % based on 1 mol of N-acetyl-D-glucosamine and D-glucuronic acid in the crosslinked hyaluronic acid, and wherein the crosslinked hyaluronic acid is one in which a hyaluronic acid having a molecular weight of 2,500,000 Da or more is crosslinked and in the form of particles having an average diameter of 300 to 400 μm, a degree of modification (MOD) (%) of the hyaluronic acid as represented by Equation 1 following is in the range of 1 to 7%:

16

$$\text{Degree of modification (\%)} = \text{total number of moles of crosslinking agent/total number of moles of N-acetyl-D-glucosamine)} \times 100, \text{ and} \quad [\text{Equation 1}]$$

a crosslinking ratio (CrR) as represented by Equation 2 is in the range of 0.1 to 0.2:

$$\text{Crosslinking ratio} = \text{number of moles of crosslinked crosslinking agent/number of moles of total crosslinking agent.} \quad [\text{Equation 2}]$$

7. The hyaluronic acid hydrogel filler according to claim 6, wherein the concentration of the crosslinking agent is 1 to 5 mol % based on 1 mol of N-acetyl-D-glucosamine and D-glucuronic acid in the crosslinked hyaluronic acid.

8. A prefilled syringe comprising the hyaluronic acid hydrogel filler according to claim 1.

9. A method for augmenting soft-tissue comprising injecting to a subject the hyaluronic acid hydrogel filler according to claim 1.

10. A method for improving wrinkles comprising injecting to a subject the hyaluronic acid hydrogel filler according to claim 1.

* * * * *